United States Patent
Ogura

(10) Patent No.: US 7,473,547 B2
(45) Date of Patent: Jan. 6, 2009

(54) TEST PIECE, METHOD OF AND APPARATUS FOR MANUFACTURING THE TEST PIECE AND METHOD OF AND SYSTEM FOR READING THE SAME

(75) Inventor: Nobuhiko Ogura, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 104 days.

(21) Appl. No.: 09/373,585

(22) Filed: Aug. 13, 1999

(65) Prior Publication Data

US 2002/0132232 A1    Sep. 19, 2002

(30) Foreign Application Priority Data

Aug. 14, 1998    (JP)    .............................. 1998-229557

(51) Int. Cl.
*C12M 1/34*    (2006.01)
*C12M 1/00*    (2006.01)
*C12Q 1/68*    (2006.01)
*G01N 15/06*    (2006.01)
*C07H 21/02*    (2006.01)

(52) U.S. Cl. .............. 435/287.1; 435/283.1; 435/287.2; 422/50; 422/68.1; 536/23.1

(58) Field of Classification Search .................... 435/6, 435/91.1, 283.1, 287.2, 287.1, 288.7; 436/94; 536/23.1, 24.3; 422/50, 68.1
See application file for complete search history.

(56) References Cited

U.S. PATENT DOCUMENTS

| | | | | |
|---|---|---|---|---|
| 4,673,657 A | | 6/1987 | Christian | |
| 4,877,745 A | * | 10/1989 | Hayes et al. | 436/166 |
| 4,881,439 A | * | 11/1989 | Biedermann et al. | 83/879 |
| 5,145,548 A | * | 9/1992 | Yamamoto | 156/350 |
| 5,310,650 A | | 5/1994 | McMahon et al. | |
| 5,429,807 A | * | 7/1995 | Matson et al. | 422/131 |
| 5,547,702 A | * | 8/1996 | Gleisner | 427/2.13 |
| 5,631,734 A | * | 5/1997 | Stern et al. | 356/317 |
| 5,658,737 A | | 8/1997 | Nelson et al. | |
| 5,808,554 A | * | 9/1998 | Shuminov | 340/604 |
| 6,037,186 A | * | 3/2000 | Stimpson | 436/518 |
| 6,057,100 A | * | 5/2000 | Heyneker | 435/6 |
| 2001/0019827 A1 | | 9/2001 | Dawson et al. | |

FOREIGN PATENT DOCUMENTS

| | | |
|---|---|---|
| JP | 60-104260 A | 6/1985 |
| JP | 10-507351 A | 7/1998 |
| JP | 2001-515735 A | 9/2001 |
| WO | 90/01564 | 2/1990 |
| WO | WO 98/04358 * | 2/1998 |

OTHER PUBLICATIONS

Klebe, Cytoscribing: a method for micropositioning cells and the construction of two- and three-dimensional synthetic tissues. Exp. Cell Res. 179, 362-373, 1988.*

(Continued)

*Primary Examiner*—Frank W Lu
(74) *Attorney, Agent, or Firm*—Sughrue Mion, PLLC

(57) ABSTRACT

A test piece for use in biological analysis of a sample is formed of a strip-like substrate and numbers of known specific binding agents which are different from each other and are arranged in a line at predetermined intervals in the longitudinal direction of the strip-like substrate.

15 Claims, 4 Drawing Sheets

OTHER PUBLICATIONS

Proudnikov et al., Immobilization of DNA in polyacrylamide gel for the manufacture of DNA and DNA-oligonucleotide microchips. 259, 34-41, May 1998.*

Stephens et al., Transcriptional repression of the GLUT4 and C/EBP genes in 3T3-L1 adipocytes by tumor necrosis factor-alpha. J. Biol. Chem. 266, 21839-21845, Nov. 1991.*

Foreign Office Action dated Sep. 24, 2003.

* cited by examiner

TEST PIECE, METHOD OF AND APPARATUS FOR MANUFACTURING THE TEST PIECE AND METHOD OF AND SYSTEM FOR READING THE SAME

BACKGROUND OF THE INVENTION

1. Field of the Invention

This invention relates a test piece for use in DNA analysis, immunological analysis and the like, a method of and an apparatus for manufacturing the test piece, and a method of and a system for reading the test piece, and more particularly to an improvement of a sequence of specific binding agents on the test piece.

2. Description of the Related Art

Recently, genetic engineering has been making rapid development and there has been progressing a human genome project for decoding a sequence of bases in human genomes which are as many as 100,000.

Further enzyme immunoassay which uses an antigen-antibody reaction, fluorescent antibody technique and the like are employed in diagnosis and/or investigation and research for DNAs which affect genetic diseases has been progressing. As a method of such research, microarray technique is greatly remarked.

As shown in FIG. 5, in the microarray technique, there is employed a microarray chip (sometimes called a DNA chip) comprising a membrane filter or a slide glass bearing thereon numbers of decoded cDNAs (a specific binding agent) applied thereto in a matrix pattern at a high density (at intervals of not larger than several hundred μm). For example, DNA (substance derived from an organism) which has been extracted from a cell of a normal person A and labelled with a fluorescent dye a and DNA which has been extracted from a cell of a sample B suffering from a genetic disease and labelled with a fluorescent dye b are pipetted onto the microarray chip to hybridize the DNAs from the normal person A and the sample B with the cDNAs on the microarray chip, and exciting light beams which respectively excite the fluorescent dyes a and b are caused to scan the cDNAs on the microarray chip. Then fluorescence emitted from the cDNAs upon excitation is detected by a photodetector and which cDNAs have been hybridized with the DNAs from the normal person A and the sample B is determined on the basis of the result of the detection of the fluorescence. The DNAs which are expressed or lost by the genetic disease are determined by comparison of cDNAs hybridized with the DNAs from the normal person A with those hybridized with the DNAs from the sample B.

As described above, the microarray chip is formed by applying an enormous number of cDNAs on a substrate such as a slide glass. When manufacturing the microarray chip, a needle-like coating chip is dipped in one of cDNAs and the cDNA adhering to the chip is spotted on the substrate in a predetermined position. Thereafter the coating chip is washed and dried, and then is dipped on another cDNA. These operations are repeated until all the cDNAs are applied to the substrate.

The number of cDNAs to be applied to the substrate sometimes reaches several hundreds of thousands and it takes a very long time to manufacture the microarray chip. Accordingly, the microarray chip is very expensive, which obstructs promoting investigation of DNA expression and/or application of immunoassay to screening.

SUMMARY OF THE INVENTION

In view of the foregoing observations and description, the primary object of the present invention is to provide a test piece which is easy to manufacture and easy to handle in biological analysis such as DNA analysis, immunological analysis and the like.

Another object of the present invention is to provide a method and an apparatus which facilitate manufacture of such a test piece.

When detecting a specific binding agent (e.g., cDNA) hybridized with substance derived from an organism (e.g., DNA), it is necessary to accurately two-dimensionally scan a microarray chip bearing thereon numbers of cDNAs applied thereto at a high density, which makes very expensive reading the microarray chip, and obstructs spread of DNA analysis using the microarray chip and application of the microarray chip to immunological analysis.

Accordingly, still another object of the present invention is to provide a method of and a system for reading the test piece which allows easier and less expensive biological analysis such as DNA analysis, immunological analysis and the like.

In accordance with a first aspect of the present invention, there is provided a test piece comprising a strip-like substrate bearing thereon numbers of known specific binding agents which are different from each other and are arranged in a line at predetermined intervals in the longitudinal direction of the strip-like substrate.

The known specific binding agents include various substances related to an organism such as hormones, tumor markers, enzymes, proteins, nucleic acids, antibodies, substances which can make antigen, and various substances which can be immunologically bonded or hybridized with substances derived from a sample organism such as cDNAs, mRNAs and the like. Among these substances, cDNAs are especially suitable.

The expression "substance derived from the sample organism" means substance which can be immunologically bonded or hybridized with the known specific agents on the substrate such as antibodies, antigens, substrates, DNAs, mRNAs and the like. Among these substances, DNAs are especially suitable.

The biological analysis includes, for instance, immunological analysis for detecting antigen or antibody on the basis of high specificity of antigen-antibody reaction, gene analysis or genetic diagnosis based on hybridization, and analysis such as biotin-adipin technique employing specific binding.

That the specific binding agents are arranged in a line need not be limited to that the specific binding agents are arranged in a continuous line but may include that the agents are arranged as fine dots along a line, for instance, by use of an ink jet mechanism. The specific binding agents may be applied (especially fixed) to the strip-like substrate in any way including coating, spraying and the like.

Preferably the strip-like substrate is a flexible member in a continuous length from the viewpoint of ease of manufacture and mass productivity.

In accordance with a second aspect of the present invention, there is provided a method of manufacturing a test piece comprising a strip-like substrate bearing thereon numbers of known specific binding agents which are different from each other and are arranged in a line at predetermined intervals in the longitudinal direction of the strip-like substrate, the method comprising the steps of applying the known specific binding agents on a sheet-like substrate in lines which extend in a first direction and are arranged at predetermined intervals in a second direction substantially perpendicular to the first direction, and cutting the sheet-like substrate bearing thereon the specific binding agents in the second direction into a plurality of strips.

In accordance with a third aspect of the present invention, there is provided an apparatus for manufacturing a test piece comprising a strip-like substrate bearing thereon numbers of known specific binding agents which are different from each other and are arranged in a line at predetermined intervals in the longitudinal direction of the strip-like substrate, the apparatus comprising numbers of application means which are arranged at predetermined intervals in a second direction relatively to a sheet-like substrate and respectively apply the known specific binding agents on the sheet-like substrate, a conveyor means which conveys the application means and the sheet-like substrate relatively to each other in a first direction substantially perpendicular to the second direction while the applications means are applying the known specific binding agents, thereby applying the known specific binding agents in lines which extend in the first direction and are arranged at predetermined intervals in the second direction, and a cutting means which cuts the sheet-like substrate bearing thereon the specific binding agents in the second direction into a plurality of strips.

In accordance with a fourth aspect of the present invention, there is provided a method of reading a test piece comprising a strip-like substrate bearing thereon numbers of known specific binding agents which are different from each other and are arranged in a line at predetermined intervals in the longitudinal direction of the strip-like substrate, the method comprising the steps of applying substance derived from a sample organism labelled with fluorescent dye to the test piece, projecting exciting light, which excites the fluorescent dye, onto the test piece applied with the substance derived from the sample organism, and detecting fluorescence emitted from the test piece upon excitation by the exciting light in relation with the positions in which the fluorescence is emitted, thereby determining the specific binding agent(s) on the test piece with which the substance derived from the sample organism is hybridized.

Hybridization generally means formation of double strands between DNA fragments having complementary base sequences but in this specification, the term "hybridization" should be broadly interpreted to include specific binding.

Projection of the exciting light and detection of the fluorescence may be carried out by causing the exciting light to linearly scan the strip-like test piece in the longitudinal direction thereof and detecting fluorescence emitted from the respective specific binding agents in sequence, or by uniformly exposing the entire surface of the test piece to exciting light which spreads at least linearly and detecting fluorescence emitted from the respective specific binding agents by, for instance, a linear CCD. However the former arrangement is advantageous over the latter arrangement in that, in the latter arrangement, the exposure area to the exciting light must be widened and the detecting area of the CCD must be widened as the length of the test piece increases, which enlarges the reading apparatus. Causing the exciting light to linearly scan the strip-like test piece may be carried either by moving the exciting light in the longitudinal direction of the test piece with the test piece kept stationary or by conveying the test piece in the longitudinal direction thereof with the exciting light fixed. The exciting light may be moved in the longitudinal direction of the test piece by moving the source of the exciting light or by deflecting the exciting light emitted from the source by a scanning optical system with the source kept stationary. However, it is preferred that the exciting light be caused to scan the test piece by conveying the test piece in the longitudinal direction thereof from the viewpoint of easiness of operation.

Detecting fluorescence emitted from the test piece upon excitation by the exciting light in relation with the positions in which the fluorescence is emitted is equivalent to determining the positions on the test piece where the fluorescence is emitted or determining the specific binding agents which emit the fluorescence. When the exciting light is caused to linearly scan the test piece, the fluorescence emitted from the test piece upon excitation by the exciting light may be detected in relation with the scanning positions of the exciting light instead of the positions in which the fluorescence is emitted.

In the method of reading the test piece in accordance with a fifth aspect of the present invention, substances derived from cells of a pair of different sample organisms are compared with each other.

That is, in accordance with the fifth aspect of the present invention, there is provided a method of reading a test piece comprising a strip-like substrate bearing thereon numbers of known specific binding agents which are different from each other and are arranged in a line at predetermined intervals in the longitudinal direction of the strip-like substrate, the method comprising the steps of applying substances derived from at least a pair of different sample organisms labelled with different fluorescent dyes to the test piece, projecting exciting light, which excites the fluorescent dyes, onto the test piece applied with the substances derived from the sample organisms, detecting fluorescence emitted from the test piece upon excitation by the exciting light in relation with the positions in which the fluorescence is emitted, thereby determining the specific binding agent(s) on the test piece with which the substance derived from each of the sample organisms is hybridized, and determining the difference between the substances derived from the respective sample organisms by comparing the specific binding agents with which the substances derived from the respective sample organisms are hybridized with each other.

The fluorescent dyes are preferably those whose emission wavelength bands do not overlap each other. However the fluorescent dyes may be those whose emission wavelength bands partly overlap each other provided that their emission wavelength bands do not overlap each other in a main detecting wavelength band.

The exciting light which excites the fluorescent dyes may comprise a plurality of light beams which are different from each other in wavelength band or a single light beam when the excitation wavelength bands of the fluorescent dyes are close to each other. When a plurality of exciting light beams are employed, the exciting light beams may be either projected simultaneously or in sequence.

In accordance with a sixth aspect of the present invention, there is provided a system for carrying out the method in accordance with the fourth aspect of the present invention. That is, in accordance with the sixth aspect of the present invention, there is provided a system for reading a test piece comprising a strip-like substrate bearing thereon numbers of known specific binding agents which are different from each other and are arranged in a line at predetermined intervals in the longitudinal direction of the strip-like substrate, the system comprising an exciting light source which projects, onto the test piece applied with substance derived from a sample organism labelled with fluorescent dye, exciting light which excites the fluorescent dye, a photodetector which detects fluorescence emitted from the test piece upon excitation by the exciting light, and an analysis means which relates the result of detection of the fluorescence with the positions in which the fluorescence is emitted and thereby determines the specific binding agent(s) on the test piece with which the substance derived from the sample organism is hybridized.

It is preferred from the viewpoint of miniaturization of the system that the system be provided with a scanning means which causes the exciting light to linearly scan the test piece, thereby exposing the specific binding agents to the exciting light in sequence, and the photodetector be arranged to detect the fluorescence emitted from the respective specific binding agents in sequence. It is preferred that the scanning means be arranged to cause the exciting light to scan the test piece by conveying the test piece in the longitudinal direction thereof from the viewpoint of easiness of operation.

In accordance with a seventh aspect of the present invention, there is provided a system for carrying out the method in accordance with the fifth aspect of the present invention. That is, in accordance with the seventh aspect of the present invention, there is provided a system for reading a test piece comprising a strip-like substrate bearing thereon numbers of known specific binding agents which are different from each other and are arranged in a line at predetermined intervals in the longitudinal direction of the strip-like substrate, the system comprising an exciting light source which projects, onto the test piece applied with substances derived from at least a pair of different sample organisms labelled with different fluorescent dyes, exciting light which excites the fluorescent dyes, a photodetector which detects fluorescence emitted from the respective fluorescent dyes upon excitation by the exciting light, and an analysis means which relates the result of detection of the fluorescence with the positions in which the fluorescence is emitted, thereby determining the specific binding agent(s) on the test piece with which the substance derived from each of the sample organisms is hybridized, and determines the difference between the substances derived from the respective sample organisms on the basis of the specific binding agents with which the substances derived from the respective sample organisms are hybridized with each other.

The exciting light source may comprise a plurality of light sources which emit a plurality of exciting light beams which are different from each other in wavelength band or may comprise a single light source when the excitation wavelength bands of the fluorescent dyes are close to each other. Further the exciting light source may comprise a single light source which emits exciting light having a wide wavelength band and optical elements such as band pass filters which are selectively inserted into the optical path of the exciting light emitted from the light source to transmit only components corresponding to the excitation wavelength of each of the fluorescent dyes. When a plurality of exciting light beams are employed, the exciting light beams may be either projected simultaneously or in sequence. In the former case, a plurality of photodetectors may be employed to separately detect the fluorescence from the respective fluorescent dyes and in the latter case, a single photodetector may detect the fluorescence from the respective fluorescent dyes in sequence.

With the test piece of the present invention, since the specific binding agents are arranged in a line, the test piece has only to be scanned linearly. which makes the test piece easy to handle.

Further the test piece of the present invention can be manufactured quickly and easily by applying the known specific binding agents on a sheet-like substrate in lines which extend in a first direction and are arranged at predetermined intervals in a second direction substantially perpendicular to the first direction, and cutting the sheet-like substrate bearing thereon the specific binding agents in the second direction into a plurality of strips.

Further when reading the test piece, the exciting light has only to scan linearly scan the test piece and need not scan the test piece two-dimensionally, which eliminates necessity to use an expensive two-dimensional scanning system and reduces the cost of DNA analysis.

Further such reduction of cost makes it feasible application of the test piece to screening of a human or an animal infected with pathogenic bacterias or viruses, screening of cancerous cells, and the like.

DESCRIPTION OF THE PREFERRED EMBODIMENTS

Figure 1:
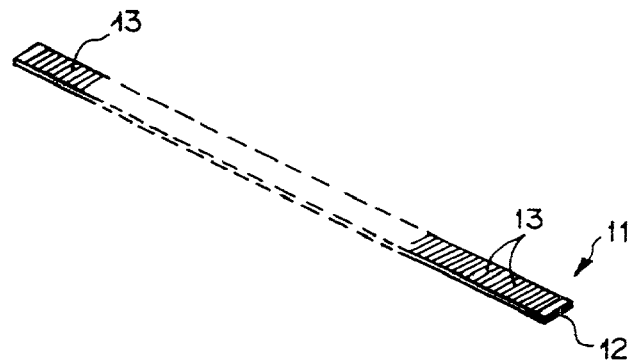
FIG. 1 is a perspective view of a test piece in accordance with an embodiment of the present invention.
Figure 2:
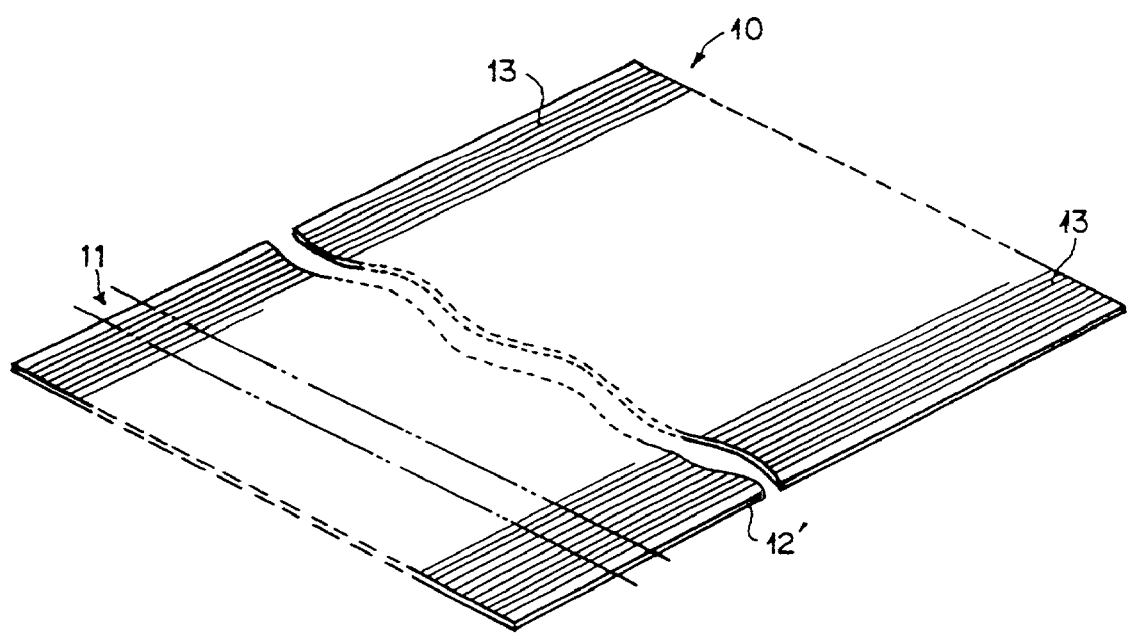
FIG. 2 is a perspective view showing an array sheet from which the test piece shown in FIG. 1 is cut.

In FIG. 1, a test piece 11 in accordance with an embodiment of the present invention comprises a transparent and flexible strip-like substrate 12 bearing thereon numbers of known cDNAs (specific binding agents) 13 which are different from each other and are arranged in a line at predetermined intervals (e.g., several hundreds of µm) in the longitudinal direction of the strip-like substrate 12. The test piece 11 is obtained, for instance, by applying the known cNDAs 13 on a transparent and flexible sheet-like substrate 12' (FIG. 2) in lines which extend in a first direction and are arranged at predetermined intervals in a second direction substantially perpendicular to the first direction, thereby forming an array sheet 10, and cutting the array sheet 10 in the second direction into a plurality of strips. The cDNAs 13 correspond to different DNAs whose base sequences have been decoded and are applied to the sheet-like substrate 12' in predetermined positions.

Since the cDNAs 13 are linearly positioned on the test piece 11, DNA analysis to be described later can be carried by linearly scanning the test piece 11, which makes the test piece 11 to be easy to handle. Further the test piece 11 can be easily manufactured in a large number by cutting the array sheet 10 which is obtained by applying the known cNDAs 13 on a sheet-like substrate 12' in lines which extend in one direction and are arranged at predetermined intervals in a direction substantially perpendicular to said one direction.

Figure 3:
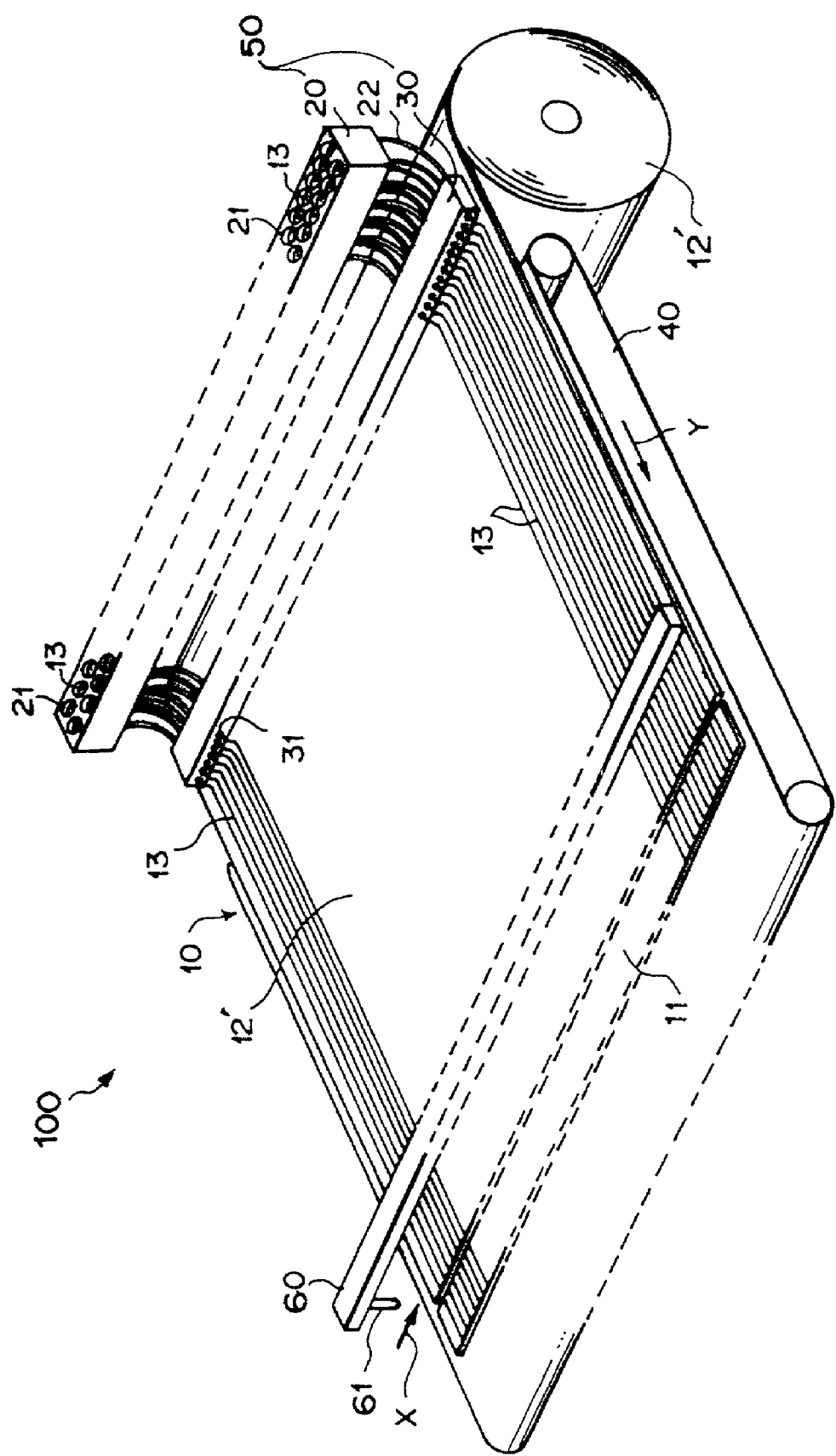
FIG. 3 is a schematic perspective view showing an apparatus for making a test piece in accordance with the present invention.

An embodiment of an apparatus for manufacturing the test piece 11 shown in FIG. 1 will be described with reference to FIG. 3, hereinbelow. In FIG. 3, a test piece manufacturing apparatus 100 comprises a conveyor belt 40 which rolls out the sheet-like substrate 12' from a sheet roll and conveys the sheet-like substrate 12' at a constant speed in the direction of arrow Y, and an applicator means 50 comprising an applicator section 30 having a number of application ports 31 arranged at predetermined intervals in the direction of width of the sheet-like substrate 12' and a supply section 20 having the same number of cDNA reservoirs 21 which are respectively connected to the application ports 31. The apparatus 100 is further provided with a cutter which cuts the substrate 12' in the direction of width thereof into a plurality of strips and comprises a guide rail 60 extending in the direction of arrow X substantially perpendicular to the direction of conveyance of the substrate 12' (direction of arrow Y) and a cutter edge 61 which is moved along the guide rail 60.

Operation of the apparatus 100 will be described, hereinbelow. The conveyor belt 40 runs in the direction of arrow Y at a constant speed with the leading end of the sheet-like substrate 12' placed thereon. While the substrate 12' is thus rolled out from the roll and conveyed in the direction of arrow Y, the cDNAs 13 are supplied to the applications ports 31 from the cDNA reservoirs 21 and applied to the substrate 12', whereby the cDNAS 13 are applied to the substrate 12' in lines which extend in the direction of conveyance of the substrate 12' (direction of arrow Y) and are arranged at regular intervals in the direction of width of the substrate 12' (direction of arrow X).

The array sheet 10 thus formed is further conveyed by the conveyor belt 40 and is cut into a plurality of strips, i.e., strip-like test pieces 11 by the cutter edge 61 which is moved in the direction of width of the substrate 12'.

The cutter edge 61 is moved at a sufficiently high speed relatively to the speed at which the substrate 12' is conveyed by the conveyor belt 40 so that the substrate 12' is cut substantially perpendicularly to the direction in which the lines of cDNAs 13 extend.

By repeating these operations, a large number of test pieces 11 can be easily manufactured in a short time.

Figure 4:
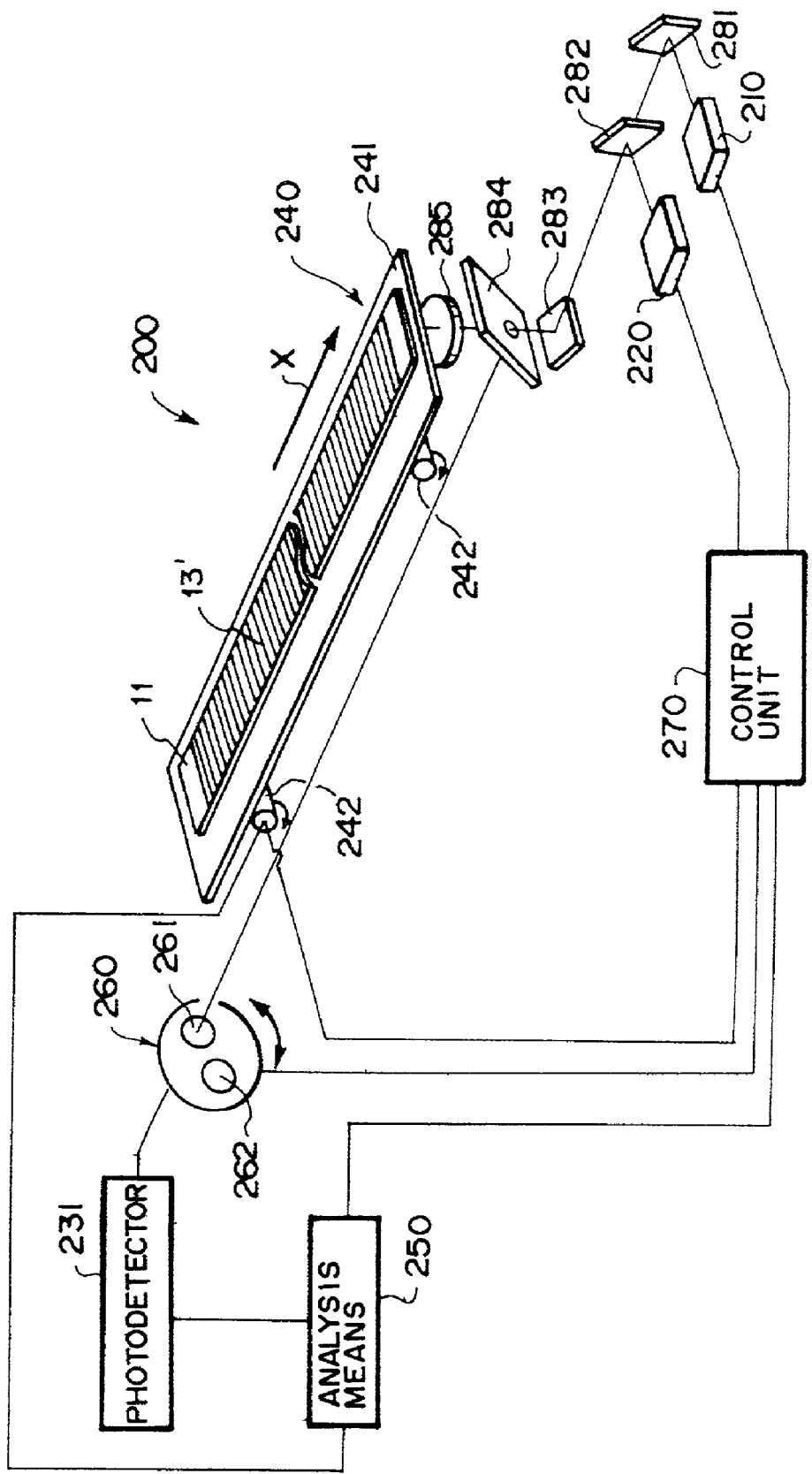
FIG. 4 is a schematic view showing a system for reading the test piece in accordance with an embodiment of the present invention.
Figure 5:
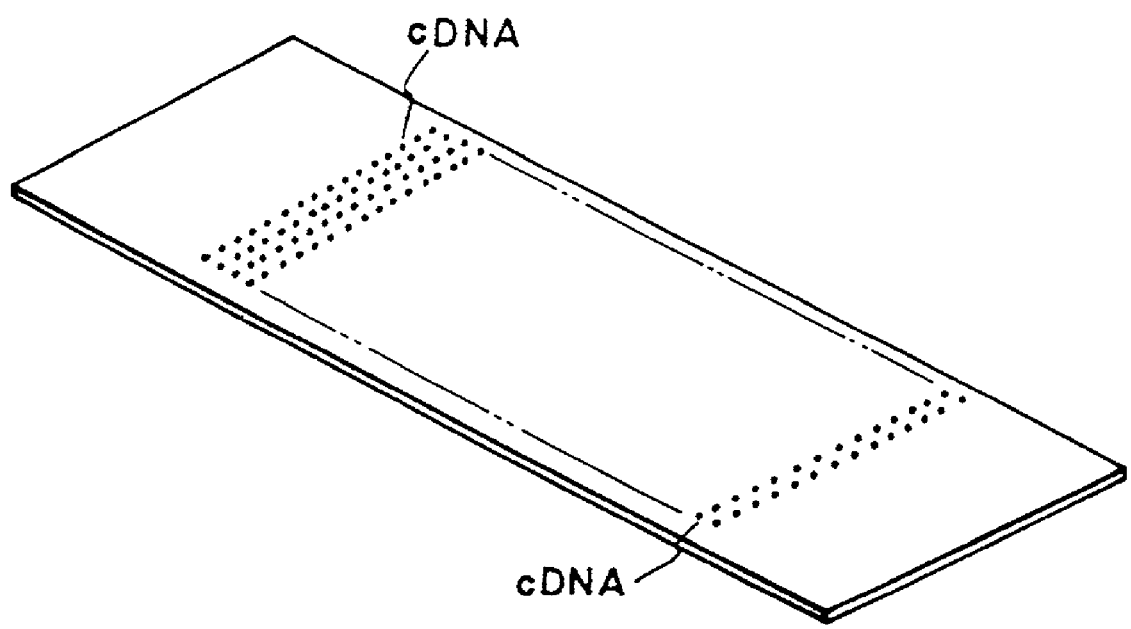
FIG. 5 is a perspective view showing a conventional test piece (microarray chip).

A system for reading a test piece in accordance with an embodiment of the present invention will be described with reference to FIG. 4, hereinbelow. The system 200 shown in FIG. 4 is for carrying out the method in accordance with the fifth aspect of the present invention. That is, the system 200 comprises a scanning means 240 which conveys a test piece 11, in the longitudinal direction thereof, which has been applied with DNAs derived from first and second sample organisms A (a normal person) and B (a patient suffers from a genetic disease) labelled with first and second fluorescent dyes a and b, first and second exciting light sources 210 and 220 which emit exciting light beams which respectively excite the fluorescent dyes a and b, an optical system which leads the exciting light beams to the test piece 11, a photodetector 230 which detects fluorescence emitted from the respective fluorescent dyes a and b upon excitation by the exciting light beams, a filter 260 which selectively permits fluorescence emitted from the respective fluorescent dyes a and b to impinge upon the photodetector 230, an analysis means 250 which determines cDNAs 13' on the test piece 11 with which the DNAs from the first and second sample organisms A and B are hybridized on the basis of the result of detection of the fluorescence and the scanning positions by the scanning means 240 in which the fluorescence is emitted, and determines the difference between the DNAs from the respective sample organisms A and B on the basis of the cDNAs 13', and a control unit 270 which switches the exciting light sources 210 and 220 and the filter 260.

The fluorescent dyes a and b are those whose emission wavelength bands do not overlap each other and whose excitation wavelength bands do not overlap each other.

DNAs extracted from cells of the respective sample organisms A and B are applied, for instance, pipetted to the cDNAs 13 on the test piece 11 and as a result, cDNAs 13' having base sequences complementary to those of the DNAs from the respective sample organisms A and B are hybridized with the DNAs. Then the cDNAs which were not hybridized with any one of the DNAs are washed off with a predetermined solution with the cDNAs 13' which have been hybridized with at least one of the DNAs left on the test piece 11.

The exciting light beam emitted from the first exciting light source 210 excites the first fluorescent dye a and the exciting light beam emitted from the second exciting light source 220 excites the second fluorescent dye b. The wavelength bands of these exciting light beams do not overlap each other.

The scanning means 240 comprises a movable table 241 on which the test piece 11 is placed and drive rollers 242 which drive the movable table 241 in the longitudinal direction of the test piece 11. The movable table 241 is formed of material which is transparent to the exciting light beams emitted from the first and second light sources 210 and 220.

The optical system which leads the exciting light beams to the test piece 11 comprises a mirror 281 which reflects the first exciting light beam emitted from the first light source 210, a dichroic mirror 282 which transmits the first exciting light beam and reflects the second exciting light beam emitted from the second light source 220, a mirror 283 which reflects both the first and second exciting light beams, a mirror 284 which is provided with a small opening, through which the exciting light beam reflected by the mirror 283 passes through the mirror 284 toward the movable table 241, and reflects fluorescence emitted from the first fluorescent dye a and fluorescence emitted from the second fluorescent dye k, and a condenser lens 285 which converges the exciting light beam passing through the small opening in the mirror 282 on the surface of the test piece 11.

The filter 20 is provided with a first section 261 which transmits only the fluorescence from the first fluorescent dye a and a second section 262 which transmits only the fluorescence from the second fluorescent dye b.

Operation of the reading system 200 will be described hereinbelow.

The movable table 241 with the test piece 11 thereon is moved in the longitudinal direction of the test piece 11 (the direction of arrow x) by the drive rollers 242 under the control of the control unit 270.

At the same time, the control unit 270 causes the first exciting light source 210 to emit the first exciting light beam. The first exciting light beam is reflected by the mirror 281, passes through the dichroic mirror 282, is reflected by the mirror 283, and passes through the small opening in the mirror 284. Then the first exciting light beam is converged on the test piece 11 through the transparent movable table 241 by the condenser lens 285.

Since the test piece 11 is being moved in the direction of arrow X, the cDNAs 13' on the test piece 11 are exposed to the first exciting light in sequence, and out of the cDNAs 13', those hybridized with the DNAs labelled with the first fluorescent dye a (DNAs from the first sample organism A) emits fluorescence since the first fluorescent dye a is excited by the first exciting light beam.

The fluorescence passes through the condenser lens 285, is reflected by the mirror 284, passes through the first section 261 and impinges upon the photodetector 231. The photodetector 231 detects the fluorescence and inputs information on the fluorescence into the analysis means 250. Information on the position of the cDNA 13' is also input into the analysis means 250 and the fluorescence is related with the cDNA 13' which emits the fluorescence.

In this manner, the cDNAs 13' which emit fluorescence upon excitation by the first exciting light beam, that is, the cDNAs 13' which are hybridized with the DNAs expressed in the cell of the first sample organism A, are determined.

Then the control unit 270 switches the first section 261 of the filter 260 to the second section 262 and switches the first exciting light source 210 to the second exciting light source 220. Then the same operation is carried out.

That is, the movable table 241 with the test piece 11 thereon is moved in the longitudinal direction of the test piece 11 by the drive rollers 242 under the control of the control unit 270.

At the same time, the control unit 270 causes the second exciting light source 220 to emit the second exciting light beam. The second exciting light beam is reflected by the dichroic mirror 282, is reflected by the mirror 283, and passes through the small opening in the mirror 284. Then the second exciting light beam is converged on the test piece 11 through the transparent movable table 241 by the condenser lens 285.

The cDNAs 13' on the test piece 11 are exposed to the second exciting light in sequence, and out of the cDNAs 13', those hybridized with the DNAs labelled with the second fluorescent dye b (DNAs from the second sample organism B) emits fluorescence since the second fluorescent dye b is excited by the second exciting light beam.

The fluorescence passes through the condenser lens 285, is reflected by the mirror 284, passes through the first section 261 and impinges upon the photodetector 231. The photodetector 231 detects the fluorescence and inputs information on the fluorescence into the analysis means 250. Information on the position of the cDNA 13' is also input into the analysis means 250 and the fluorescence is related with the cDNA 13' which emits the fluorescence.

In this manner, the cDNAs 13' which emit fluorescence upon excitation by the second exciting light beam, that is, the cDNAs 13' which are hybridized with the DNAs expressed in the cell of the second sample organism B, are determined.

Then the analysis means 250 compares with the cDNAs 13' determined for the first sample organism A with those determined for the second sample organism B and obtains the difference therebetween. Since the kinds and sequence of the cDNAs on the test piece 11 are known, the analysis means 250 can determine the cDNAs which exist in the first sample organism A and do not exist in the second sample organism B and those which do not exist in the first sample organism A and exist in the second sample organism B. Accordingly, the DNAs related to the genetic disease which the patient (second sample organism B) suffers from can be determined.

Thus, when the test piece 11 of the present invention is employed in the DNA analysis, the DNAs related to the genetic disease which the patient suffers from can be determined by only linearly scanning the test piece 11. Accordingly, the DNA analysis can be effected at a lower cost than in the conventional system where the microarray chip is two-dimensionally scanned by a two-dimensional scanning system which is expensive.

Though the reading system 200 of this embodiment is for comparing gene information on a plurality of sample organisms, it may be employed for DNA analysis of a single sample organism. In such a case, only a single exciting light source and a single filter are required.

Further instead of moving the test piece 11 (i.e., movable table 241), the mirrors 283 and 284 and the condenser lens 284 may be moved in the longitudinal direction of the test piece 11.

Further though in the embodiments described above, cDNAs are employed as the specific binding agents and DNAs are employed as the substance derived from an organism, other specific binding agents and other substances derived from an organism may be employed.

What is claimed is:

1. An apparatus for manufacturing a test piece for use in biological analysis of a sample organism comprising a strip-like substrate bearing thereon numbers of known specific binding agents which are different from each other and are arranged in a line at predetermined intervals in the longitudinal direction of the strip-like substrate, the apparatus comprising:
a plurality of applicators arranged at predetermined interval in a first direction relative to a sheet-like substrate each of said plurality of applicators respectively operable to apply one of the plurality of known specific binding agents on the sheet-like substrate,
a conveyor which conveys the plurality of applicators or the sheet-like substrate relative to each other in a second direction which is substantially perpendicular to the first direction while the applicators apply the plurality of known specific binding agents, thereby applying the plurality of known specific binding agents in lines which extend in the second direction and are arranged at predetermined intervals in the first direction, and
a cutting means which cuts the sheet-like substrate bearing thereon the plurality of specific binding agents in the first direction into a plurality of strips.

2. The apparatus as defined in claim 1 in which said specific binding agents are cDNA's.

3. The apparatus of claim 1, wherein the binding agents are formed in continuous lines across the sheet-like substrate.

4. The apparatus according to claim 1, wherein each of said plurality of applicators synchronously apply the plurality of known specific binding agents on the sheet-like substrate.

5. The apparatus according to claim 1, wherein said conveyor comprises a conveyor belt, wherein said conveyor belt continuously conveys said strip-like substrate.

6. The apparatus according to claim 1, wherein said cutting means comprises:
a guide rail; and
a cutting edge;
wherein said cutting edge moves along said guide rail.

7. The apparatus according to claim 1, wherein said predetermined intervals comprise a fixed number of intervals.

8. An apparatus for manufacturing a test piece according to claim 2, wherein the plurality of known specific binding agents applied in a line comprise a plurality of dots.

9. An apparatus for manufacturing a test piece according to claim 2, wherein said substrate is transparent.

10. An apparatus for manufacturing a test piece according to claim 2, that apparatus comprising a flat surface accommodating the sheet-like substrate.

11. The apparatus according to claim 6, wherein said guide rail forms an upper body portion of said cutting means.

12. The apparatus according to claim 1, wherein said binding agents are arranged on the surface of the strip-like substrate in the longitudinal direction of the strip-like substrate.

13. The apparatus according to claim 1, wherein said cutting means cuts the sheet-like substrate in a direction perpendicular to the longitudinal direction of the strip-like substrate.

14. The apparatus according to claim 1, wherein the first direction is perpendicular to the longitudinal direction of the strip-like substrate.

15. An apparatus for manufacturing a test piece for use in biological analysis of a sample organism comprising a strip-like substrate bearing thereon numbers of known specific binding agents which are different from each other and are arranged in a line at predetermined intervals in the longitudinal direction of the strip-like substrate, the apparatus comprising:

a plurality of applicator means arranged at predetermined interval in a first direction relative to a sheet-like substrate each of said plurality of applicators respectively operable to apply one of the plurality of known specific binding agents on the sheet-like substrate, a conveyor means which conveys the plurality of applicators or the sheet-like substrate relative to each other in a second direction which is substantially perpendicular to the first direction while the applicators apply the plurality of known specific binding agents, thereby applying the plurality of known specific binding agents in lines which extend in the second direction and are arranged at predetermined intervals in the first direction, and a cutting means which cuts the sheet-like substrate bearing thereon the plurality of specific binding agents in the first direction into a plurality of strips.

* * * * *